Figure 1:
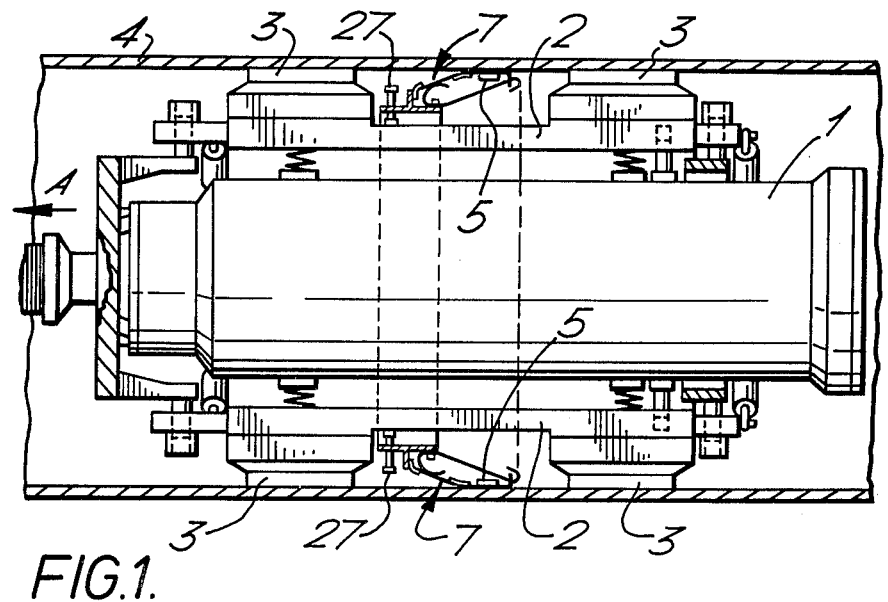

United States Patent [19]

Smith

[11] 4,105,972
[45] Aug. 8, 1978

[54] PIPELINE INSPECTION VEHICLE FOR DETECTING DEFECTS IN PIPELINE WALLS

[75] Inventor: Ian Smith, Ashington, England

[73] Assignee: British Gas Corporation, England

[21] Appl. No.: 784,911

[22] Filed: Apr. 5, 1977

[30] Foreign Application Priority Data

Apr. 9, 1976 [GB] United Kingdom ............... 14555/76

[51] Int. Cl.² .................................................. G01R 33/12
[52] U.S. Cl. ................................. 324/220; 324/242;
350/358; 73/638
[58] Field of Search ............. 324/37, 40, 67, 240–242, 324/219–221; 73/49.1, 49.5, 638, 432 R; 16/DIG. 3; 308/2; 248/280; 350/358 P

[56] References Cited

U.S. PATENT DOCUMENTS

| | | | |
|---|---|---|---|
| 2,435,985 | 2/1948 | Stewart et al. | 324/34 R |
| 3,066,254 | 11/1962 | Price et al. | 324/37 |
| 3,281,660 | 10/1966 | Studenick | 324/34 R |
| 3,529,236 | 9/1970 | Proctor | 324/37 |
| 3,593,122 | 7/1971 | Barton | 324/37 |
| 3,786,684 | 1/1974 | Wiers et al. | 324/37 |

*Primary Examiner*—Robert J. Corcoran
*Attorney, Agent, or Firm*—Watson, Cole, Grindle & Watson

[57] ABSTRACT

A pipeline inspection vehicle for detecting defects in the pipeline wall provided with a detector support system comprising a freely supported ring encircling the body of the vehicle and on which are mounted a plurality of spring-loaded pivotally connected link plates, the outermost plates of which carry flux-sensing devices and are urged by spring means resiliently to engage the inner surface of the pipeline wall.

9 Claims, 4 Drawing Figures

PIPELINE INSPECTION VEHICLE FOR DETECTING DEFECTS IN PIPELINE WALLS

This invention relates to pipeline inspection vehicles (commonly known as a pipeline pig) which can be inserted into a pipeline of ferro-magnetic material and carried along by the fluid flow in the pipeline for detecting defects in the pipeline wall.

Pipeline inspection vehicles or pigs of the kind with which the present invention is particularly concerned usually include a system for supporting a number of defect-detection devices, for example magnetic flux sensors, arranged during movement of the pig along the pipeline under test, to produce signals representative of the resultant variation in the magnetic properties of the pipeline. These defect-indicating signals can subsequently be interpreted into data representative of the mechanical and physical condition of the pipeline.

Some detection device support systems which have been tired to date employ large heavy cast metal shoes mounted on the body of the inspection vehicle and spring-loaded into contact with the pipe wall (typically 12 shoes each having 20 sensors mounted in them). This arrangement however, suffers many disadvantages in that dynamic lift-off of the heavy shoes at each girth weld of the pipeline sections is large and of long duration, and the weight of each shoe contributes to mechanical damage of the shoe and shoe support particularly at branch pipe cut-out regions of the pipe wall. Also, at least one shoe will run along the longitudinal seam weld of the pipeline resulting in static-lift-off of a large number of sensors. Also, since the curvature of each shoe is fixed, it cannot conform to changes in pipe wall curvature from the normal caused by changes in wall thickness of different sections of the pipeline. These changes also result in static sensor lift-off. Furthermore, in order to obtain full circumferential coverage of the pipe wall, two staggered rows of shoes are normally required and this leads to difficulties in signal interpretation.

Work has been carried out to devise an improved system of supporting the defect-detection devices of a pipeline inspection vehicle.

According to the invention, in a pipeline inspection vehicle for detecting defects in pipeline walls, there is provided a system for supporting a plurality of defect-detector modules comprising a plurality of sledge units upon which the detector devices are mounted, a ring member disposed around but spaced from the vehicle to which it is connected arranged to carry the sledge units in circumferential side-by-side relationship with each other around the ring member, and means for connecting the ring member of the body of the vehicle, each sledge unit comprising two or more links connected together for pivotal movement with respect to each other, one of said links being arranged to carry a detector module whilst the link remote from said detector module-carrying link being pivotally connected to the ring member, and spring means arranged in use of the vehicle to urge at least the detector module-carrying link outwardly so as resiliently to engage the inner surface of the pipeline wall.

Preferably, each sledge unit consists of two links in the form of thin plates, a first plate of which carried a detector module on its underside and is pivotally connected at one end thereof by hinge means to one end of the second plate thereof which in turn is pivotally connected at its other end by further hinge means to the ring member. Then the spring means preferably consists of a leaf spring fixed by means positioned intermediate of its length to the ring member and having its free arms flexed, in use of the vehicle in the pipeline, to engage a respective one of said first and second link plates whereby the outwardly directed spring pressure applied both to said first and second link plates urges the leading and trailing edges of the first link plate against the inner surface of the pipeline wall. It will be appreciated that the spring tension supply to the first and second links can be adjusted to give the same or differential bias to the leading and trailing edges of the first link plate.

Preferably, the second link plate is engaged by the appropriate free arm of the leaf spring at a point substantially intermediate of its length, whilst the first link plate is engaged by the appropriate free arm of the leaf spring at its trailing end, preferably through an aperture formed thereat. Then the sensor module may be secured at the region of the first plate substantially intermediate of its length.

The hinge means can take any convenient form, for example, they may each consist of a well known hinge and pin device although, preferably, for cheapness, they may each consist of a short length of flexible material secured between the parts of the link plates and ring member respectively.

The means for connecting the ring member to the vehicle includes means for freely supporting it about the vehicle body, which support means can take any suitable form, for example, a towing link connected between the ring member and the vehicle body, although, preferably, the support means will consist of a plurlity of mutually engaging pin-in-slot connecting device separately associated between a part of the vehicle body and the ring member arranged, in use of the vehicle, to enable the ring member and its associated sledge units to be carried or towed along the pipeline with the vehicle but also to be freely supported about the vehicle body such that it can move in a radial plane normal to the longitudinal axis of the vehicle so as to be centralised within the bore by the combined action of the resiliently mounted sledge units engaging the internal surface of the pipeline.

At least three pin-in-slot connecting devices are provided, each of which may take the form of a radially outwardly extending post fixed to a body of the vehicle, and a circumferentially aligned slot formed in an axially extending flange portion of the ring member arranged, in use, loosely to fit over the post so that the ring member is freely supported about the vehicle body as aforesaid.

Figure 4:
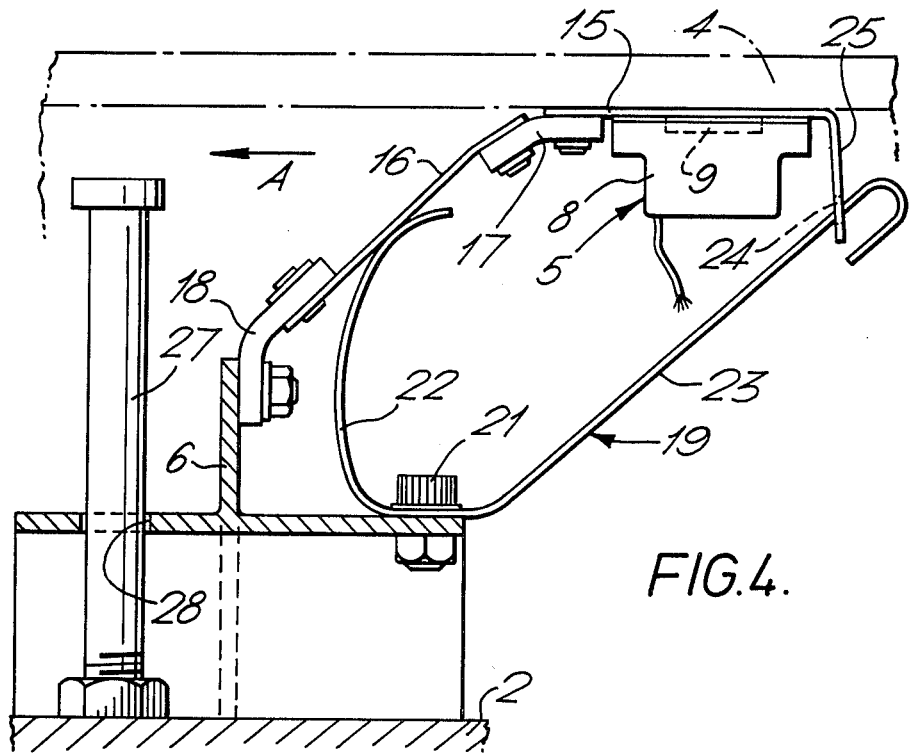
Figure 3:
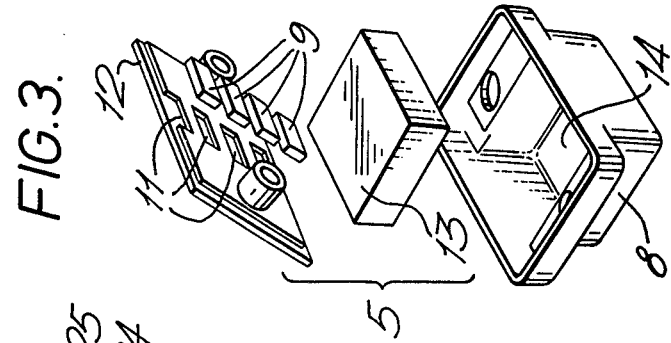
Figure 2:
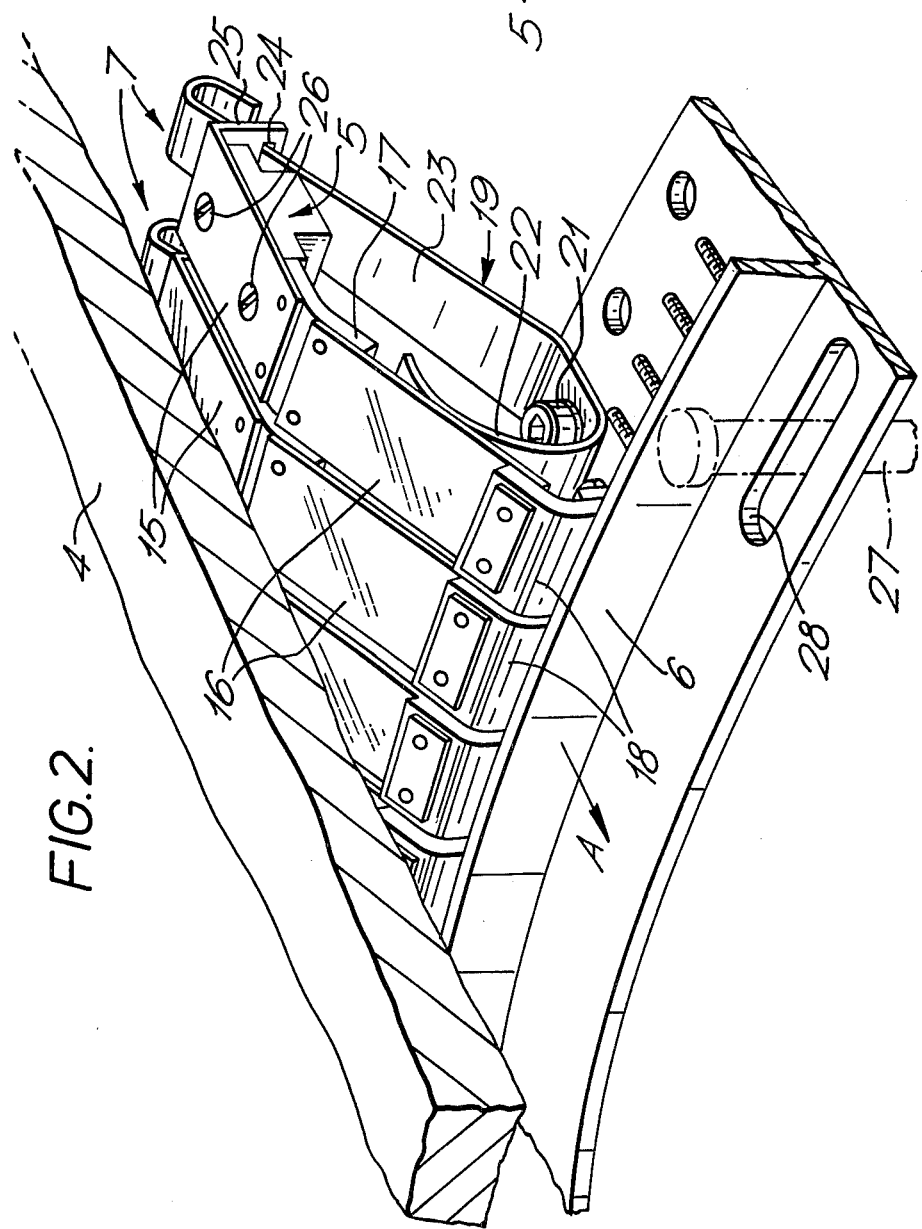

The invention will now be described by way of example with reference to the accompanying drawings in which:

FIG. 1 is a diagrammatic illustration of a pipeline inspection vehicle incorporating a pipeline defect-detecting system in accordance with the invention, FIGS. 2 and 3 show in perspective projection a practical embodiment of part of the detecting system, and FIG. 4 is a diagrammatic sectional detail of a connecting means between the detecting system and the vehicle body.

Referring first to FIG. 1, the magnetic trailer vehicle of a pipeline inspection pig consists generally of a body 1 encircled by at least six spring-loaded powerful magnet segments 2 each having pole pieces 3 which induce a relatively strong magnetic field in the region of the pipeline wall 4 under examination. The magnetic lines of force are constrained within the ferromagnetic pipeline wall, but where a fault or defect occurs there is a higher leakage field which is detected by sensors in a plurality of detector modules 5. Referring also to FIGS. 2 and 3, the vehicle carries a flanged ring 6 on which is mounted a plurality of sledge units 7 (typically sixty units on a 24-inch diameter vehicle) each carrying a module 5. Each module comprises a container 8 having an array of four sensors 9 mounted in recesses 11 in a container closure member 12. In an alternative arrangement, the magnetic field in the pipeline wall may be induced by magnets 13 in recesses 14 in each container 8.

Each sledge unit comprises a first plate 15, a second plate 16 hinged to the first plate for pivotal movement by a flexible member, for example, a rubber or rubber/fabric hinge strip 17. The second plate 16 is hinged to the flange ring 6 by a similar hinge strip 18. A shaped leaf spring 19 is fixed to the flanged ring 6 at a point intermediate its length by means of a fastening member 21.

In the use of the vehicle (as shown), the arm 22 of the spring 19 engages the second plate 16, whilst the arm 23 engages the first plate 15 through a slot 24 formed in its outer free end 25.

the modules 5 are mounted on the underside of the plate 15 by means of screws 26 with the sensors uppermost so as to be in close proximity to the pipeline wall, but protected by the plate 15 which is made as thin as is acceptable.

To enable the whole detector system to be freely supported in use as aforesaid, at least each alternate magnet segment 2, and preferably each one of the six segments, is provided with an outwardly extending post 27 detachably secured thereto. Each post is freely engaged by an associated one of a corresponding number of elongate slots 28 formed in the flanged ring 6. The slots are, of course, orientated in circumferential directions around the flanged ring so as effectively to permit the ring and its associated sensor sledges to be towed along the pipeline without any appreciable backlash, but to float in a plane at right angles to the axis of the pig such that it will centralise itself within the pipeline bore, particularly when the pig is passing through a curved portion of the pipeline.

In operation of the pig, assuming its movement through the pipeline to be in the direction of arrowheads A in the drawings, the leading edge of the link plate 15 is effectively spring-loaded into contact with the pipeline wall 4 by the spring pressure applied by the spring arm 22 to the link plate 16, whilst the trailing edge of the link plate 15 is urged into contact with the wall 4 by the spring arm 23. Thus, the whole length of the link plate 15 is maintained in contact with the pipe wall.

The sledges are sufficiently close together around the circumference of the pipeline wall to ensure full inspection coverage. The sledge system accommodates small changes in pipeline diameter and the sledges are arranged to ride easily over welds and other such obstructions, and to regain their normal operating position within a short distance of any branch cut-outs or disturbance in the pipeline. For optimum sensitivity, the sensors are as close to the surface as possible and they are sufficiently close together, i.e. having a separation in the range 5 to 10 mm around the entire circumference, not to miss a feature of significant size. Furthermore the orientation of the sensors are maintained relative to the pipeline wall in bends as well as in straight pipe.

I claim:

1. A pipeline inspection vehicle for detecting defects in pipeline walls, having a system for supporting a plurality of detector modules for detecting said defects, which system comprises, a plurality of sledge units each carrying one of said detector modules, a floating ring member disposed around but spaced from the vehicle, means for connectig said ring member about the body of said vehicle, and means for pivotally connecting the sledge units to said ring member in circumferential side-by-side relationship with each other around said ring member, each sledge unit comprising two or more links connected together for pivotal movement with respect to each other, one of said links being arranged to carry a detector module whilst the link remote from said detector module-carrying link being connected to said ring member by pivotal connecting means, and spring means connected respectively to the remote link and to the detector carrying link and arranged independently to urge the leading trailing edges of the detector module-carrying link outwardly so as to resilienly engage the inner surface of the pipeline wall.

2. A pipeline inspection vehicle according to claim 1, wherein each sledge unit is provided with two links in the form of thin plates, a first plate of which carried a detector module on its underside and is pivotally connected at one end thereof by hinge means to one end of the second plate thereof which in turn is pivotally connected at its other end by further hinge means to said ring member.

3. A pipeline inspection vehicle according to claim 2, wherein the spring means consists of a leaf spring fixed by means positioned intermediate of its length to the ring member and arranged for each of its free arms to be flexed and to engage a respective one of said first and second link plates whereby outwardly directed pressure applied by said spring means both to said first and second link plates urges the leading and trailing edges of the first link plate against the inner surface of the pipeline wall as aforesaid.

4. A pipeline inspection vehicle according to claim 3, wherein the second link plate is engaged by one free arm of the leaf spring at a point substantially intermediate of its length, whilst the first link plate is engaged by the other free arm of the leaf spring at its trailing end.

5. A pipeline inspection vehicle according to claim 4, wherein the detector module is secured at a region of the first plate substantialy intermediate of its length.

6. A pipeline inspection vehicle according to claim 2, wherein each hinge means consists of a short length of flexible material secured between parts of the link plates and ring member respectively.

7. A pipeline inspection vehicle according to claim 1, wherein the means for connecting said ring member about the vehicle body consists of a plurality of mutually engaging pin-in-slot devices, the pin and slot of each device being respectively provided on a part of the vehicle body and the ring member, the arrangement being such that in use of the vehicle, the ring member and its associated sledge units will be carried or towed along the pipeline with the vehicle but will also be freely connected about the vehicle such that it can move in a radial plane normal to the longitudinal axis of the vehicle so as to be centralised within the pipeline by the combined action of the resiliently mountedsledge units engaging the internal surface of the pipeline 8. A pipeline inspection vehicle according to claim 7, wherein at least three pin-in-slot connecting devices are provided, each of which takes the form of a radially outwardly extending post fixed to the body part of the vehicle, and a circumferentially aligned slot formedin an axially entending flange portion of the ring member arranged, in use, to loosely fit over the post so that the ring member is freely supported about the vehicle body as aforesaid.

9. A pipeline inspection vehicle according to claim 1, wherein each defect-detector module consists of a container housing an array of magnetic flux sensors spaced circumferentially with respect to the axis of the vehicle with a separation of between 5 to 10 mm between each sensor.

* * * * *